United States Patent [19]

Takeuchi

[11] 4,150,667
[45] Apr. 24, 1979

[54] ROTARY FOOT-OPERATED MASSAGING DEVICE

[76] Inventor: Toshio Takeuchi, 4-15, Takaramachi 3-chome, Kariya-shi, Japan

[21] Appl. No.: 796,465

[22] Filed: May 12, 1977

[30] Foreign Application Priority Data

May 15, 1976 [JP] Japan .............................. 51-61467[U]
Jun. 19, 1976 [JP] Japan .............................. 51-80549[U]
Jun. 22, 1976 [JP] Japan .............................. 51-82496[U]

[51] Int. Cl.² .............................................. A61H 1/02
[52] U.S. Cl. ...................................... 128/25 B; 128/57
[58] Field of Search ................... 128/25 B, 25 R, 24.3, 128/57, 56

[56] References Cited

U.S. PATENT DOCUMENTS

| | | | |
|---|---|---|---|
| 2,278,861 | 4/1942 | Burke | 128/25 R |
| 3,213,852 | 10/1965 | Zent | 128/25 R |

FOREIGN PATENT DOCUMENTS 2538034  3/1977  Fed. Rep. of Germany ........ 128/25 R

*Primary Examiner*—Lawrence W. Trapp
*Attorney, Agent, or Firm*—Blair, Brown & Kreten

[57] ABSTRACT

A rotary foot-operated massaging device having a crank shaft, a pair of pedal axles connected to the opposite ends of the crank shaft, a pedal rotatably carried by each pedal axle and a massaging member carried at least on each pedal axle. The device may either be an independent floor-mounted unit or form a part of a bicycle to also serve as a propelling unit therefor.

14 Claims, 8 Drawing Figures

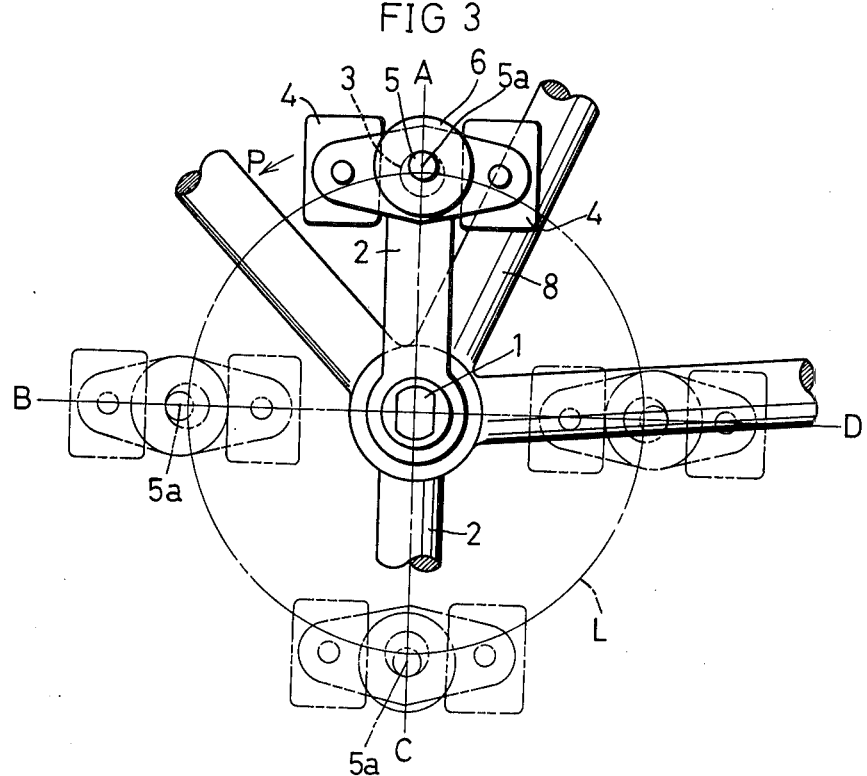
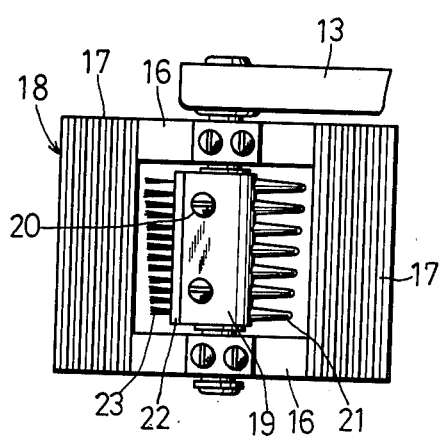
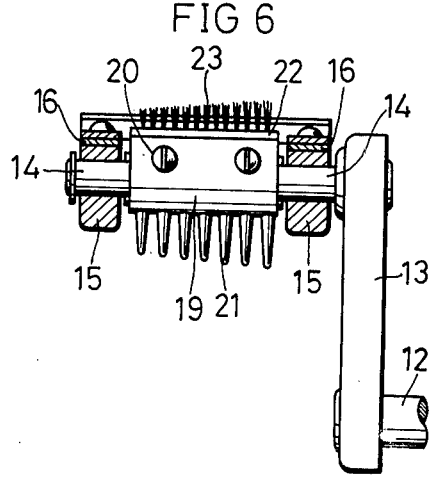

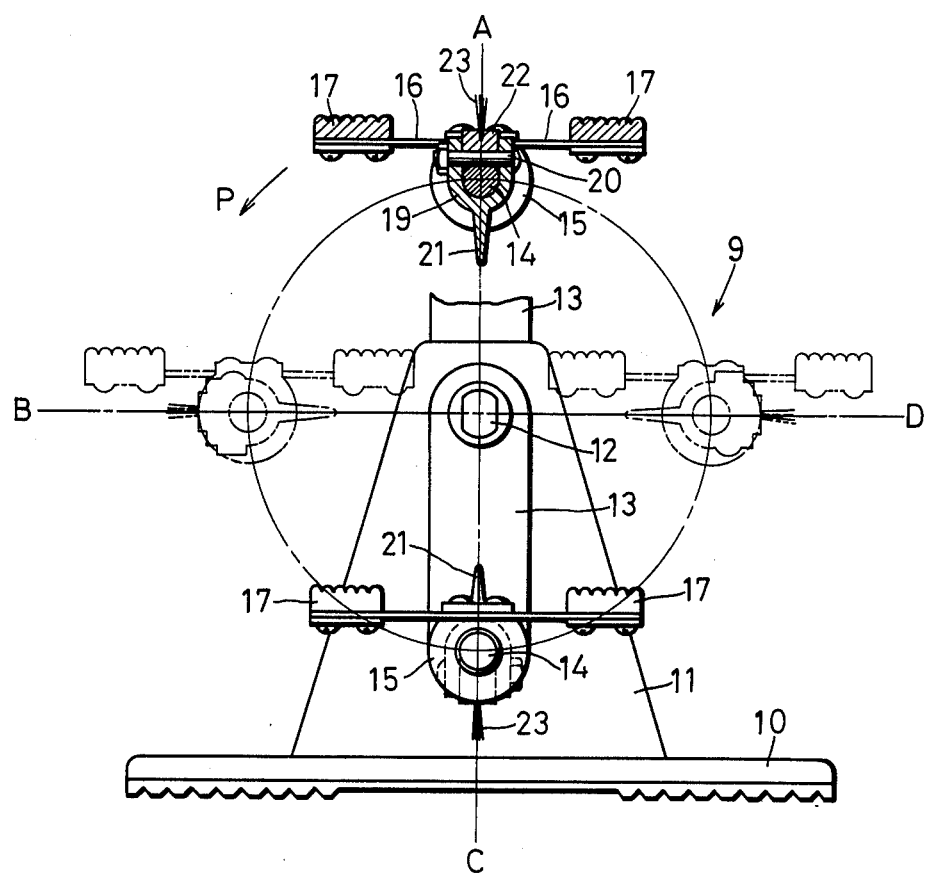

ROTARY FOOT-OPERATED MASSAGING DEVICE

This invention relates to a rotatory foot-operated massaging device.

In a human body circulation of the blood is apt to be interrupted to cause congestion at the soles of his feet because it is farthest from the heart managing the circulation of the blood. For promoting one's health an appropriate stimulus may be given to the soles of his feet to facilitate the circulation of the blood therein.

There is known a rotary foot-operated massaging device which is similar in construction to the propelling mechanism of an ordinary bicycle. This device does not have any pedal elements of the sort which the bicycle has, but in operation, a man places his feet directly on a pair of pedal axles and rotate them in such a manner as he rotates the pedals of a bicycle, whereby the soles of his feet are rubbed against the outer peripheral surface of the pedal axles. As the pedal axles rotate about their own axes, too, however, it is difficult for the user to maintain his feet in a fixed position on the pedal axles during continual revolution of the latter. He often tends to have his bare feet slip off the axles, particularly when he continues to rotate the axles in a single direction. This problem can be solved if he puts socks for improving the sliding contact between the feet and the pedal axles, but still, what he can obtain is merely continuous pressing of his soles against the axles.

The effect of massage on any portion of a human body is generally considered useful in view of the physiological function of the human body when the portion to be massaged is pressed or rubbed intermittently, rather than continuously, because the portion to be massaged does not get numb. Thus, the known device designed merely for continuous pressing or rubbing is unsatisfactory.

An object of this invention is to provide an improved rotary foot-operated massaging device for pressing and rubbing the soles of one's feet intermittently to promote the circulation of blood and lymph therein to quicken the metabolism in his body without making his feet numb.

The invention will now be described in further detail by way of example with reference to the accompanying drawings, in which:

FIG. 3 is a side elevational view showing the different positions of a massaging roller during the rotary movement of the pedal;

FIG. 4 is a side elevational view of another embodiment of this invention showing the different positions of the massaging members during the rotary movement of the pedal;

FIG. 5 is a fragmentary top plan view of the device of FIG. 4;

FIG. 6 is a fragmentary front elevational view partly in section of the device of FIG. 4;

Figure 1:
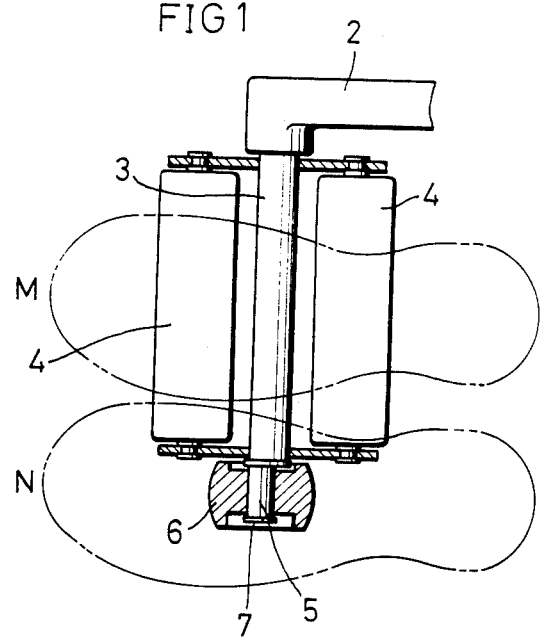
FIG. 1 is a fragmentary top plan view partly in section of the device embodying this invention.
Figure 2:
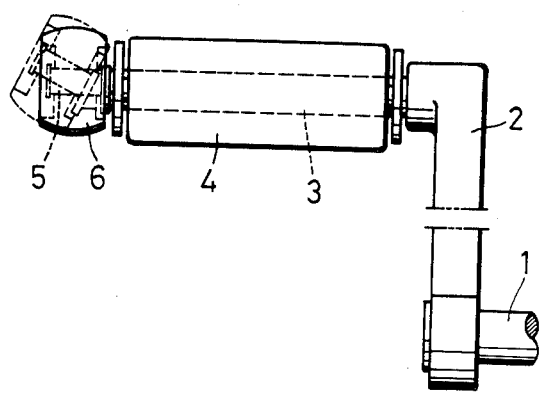
FIG. 2 is a front elevation of the device of FIG. 1.

Referring now to the drawings more specifically, FIGS. 1 through 3 show an embodiment of this invention applied to a bicycle. As is well known with an ordinary bicycle, a pair of cranks 2 are secured to the opposite ends of a bracket axle 1 at right angles thereto and extend therefrom in the opposite directions. In the drawings, only one of the cranks 2 is shown for simplifying the illustration, but it will readily be appreciated that the device of this invention is likewise used on the opposite side of the bicycle not herein shown and described. A pedal spindle 3 is secured at right angles to the free end of each crank 2 and extends in a direction opposite to that in which the bracket axle 1 extends from the crank 2. A pedal 4 is rotatably supported on the pedal spindle 3 and includes a pair of pedal elements between which the pedal spindle 3 extends. The pedal spindle 3 has a free end projecting beyond the pedal 4 and an eccentric pin 5 is secured to that free end eccentrically to the pedal spindle 3. A roller 6 is provided rotably around the eccentric shaft 5 and a collar 7 is provided at the end of said shaft 5 for preventing the roller 6 from slipping off the eccentric pin 5. The same purpose may be attained by using a separate washer in the place of the collar 7. Numeral 8 indicates a tubular seat supporting frame.

The movement of the roller 6 is described with reference to FIG. 3 in which the pedal spindle 3 is shown for rotation in the direction of an arrow P. When the pedal spindle 3 is rotated, the axis of the spindle 3 moves along a circle L shown in a chain line in FIG. 3. Therefore, when the pedal spindle 3 is at its highest position indicated at A in FIG. 3, the axis $5a$ of the eccentric shaft 5 lies above the axis of the pedal spindle 3, so that the roller 6 has an upper peripheral surface projecting above the pedal 4. As the pedal 4 is moved to a position B, displaced 90° from position A, the axis $5a$ of the eccentric shaft 5 lies in a horizontal plane common to the axis of the pedal spindle 3, so that the top surface of the roller 6 becomes substantially flush with that of the pedal 4. As the pedal 4 is further rotated to its lowest position C, the axis $5a$ of the eccentric shaft 5 is placed lower than that of the pedal spindle 3, so that the top surface of the roller 6 is placed lower than that of the pedal 4. When the pedal 4 is further moved to a position D opposite to the position B, the roller 6 is placed at the same height as in the position B and the top surface thereof becomes flush with that of the pedal 4.

When one continues to ride the bicycle for a long time, the soles of his feet become congested. In such a case, he moves his feet outwardly from the usual position M of his soles to a position N to place his plantar arches on the rollers 6. The soles of his feet may be partly left on the ends of the pedals 4, so that the bicycle may be moved ahead as usual. When the pedals 4 are rotated the rollers 6 are alternately brought into their highest position relative to the axis of the pedal spindle 3 as shown at A in FIG. 3, in which the rollers 6 press the plantar arches hard throught the soles of his shoes. As the pedal 4 is stepped down from this position A and rotated in the direction of the arrow P, the roller 6 revolves about the bracket axle 1, while rotating about the eccentric pin 5, to lower its height relative to the pedal 4 gradually to thereby rub the sole of the foot with a gradually decreasing pressure. While the pedal 4 is moved from the position B to the lowest position C, the pressure of the roller 6 working upon the sole of the foot becomes gradually smaller and at the lowest position C the pressure becomes substantially zero. While the pedal 4 is moved from the position C to the position D, the roller 6 is again raised relative to the axis of the pedal spindle 3 and begins to press the sole of the foot weakly. While the pedal 4 is moved from the position D to the highest position A, roller 6 is further raised relative to the pedal spindle 3 to rub the sole with an increasing amount of pressure and when it reaches the highest position A, it presses the sole with the strongest force.

When the pedal 4 and the roller 6 thus complete one revolution around the circle L, it will be noted that the plantar arches of the feet are pressed once and rubbed twice.

While in this embodiment, the rollers 6 are brought to the highest position relative to the pedal spindle 3 when the pedal 4 comes to the highest position, the rollers 6 may alternatively be adapted to project above the pedals 4 at any other position B (D) or C if the eccentric position of the eccentric shaft 5 relative to the pedal spindle 3 is appropriately selected.

The rollers 6 have a particular good stimulating effect on the feet wearing rubber-soled shoes. Moreover, if the eccentricity of the eccentric shaft 5 relative to the pedal spindle 3 is made greater or the diameter of the roller 6 is made greater, the pressure applied by the roller 6 upon the sole of the foot may be increased. Furthermore, the roller 6 does not necessarily have to rotate around the shaft 5, but may be fixed to the shaft 5 or formed integral with it. The roller 6 does not always need to have an axis parallel to that of the pedal spindle 3, but may also be mounted with its axis extending at an angle to that of the pedal spindle 3 as shown in a chain line in FIG. 2.

Another embodiment is shown in FIGS. 4 through 6, in which the invention is embodied in a self-supporting foot massaging device 9 comprising a base plate 10, a bearing support 11 on the base plate 11 and a horizontal crank shaft 12 mounted rotatably across the upper portion of the bearing support 11. A pair of cranks 13 are secured to the opposite ends of the crank shaft 12 and project therefrom in opposite directions. A pedal spindle 14 is secured to the free end of each crank 13 at right angles thereto. A pair of spaced-apart bosses 15 are rotatably supported on the pedal spindle 14 adjacent to the opposite ends thereof and a leaf spring 16 is secured on each boss 15 at right angles to the pedal spindle 14. Two spaced-apart pedal elements 17 made of rubber or synthetic resins are connected to the leaf springs 16 to form a rectangular pedal 18. A retainer 19 having a U-shaped cross-section is fixed about the pedal spindle 14 by two bolts 20 and surrounded by the pedal 18. A plurality of projections 21 extend outwardly from the closed end of the U-shaped retainer 19 in a line parallel to the pedal spindle 14. The projections 21 are formed of a flexible material such as rubber or synthetic resins and have a gradually increasing length toward the crank 13 as shown in FIG. 6. A brush holder 22 is secured in the open end of the retainer 19 by the bolts 20. A brush 23 is fixed to the outer edge of the brush holder 22 and composed of brush elements having a gradually increasing length toward the crank 13. The brush 23 extends outwardly from the brush holder 22 in a direction opposite to that of the projections 21. The slopes defined by the tips of the projections 21 and the brush 23 are substantially complementary to the curvature of the plantar arch of one's foot.

Operation of the second embodiment is explained. A man sits on an appropriate chair or the like and takes off his shoes. He places one of his feet on each pedal 18 and presses on the pedals 18 to rotate the crank shaft 12 in the same manner as when he rides a bicycle. When the crank shaft 12 is rotated the pedals 18 are rotated around the crank shaft 12. During such rotation, the pedals 18 are maintained in a substantially horizontal position, but the projections 21 and the brush 23 rotate about the pedal spindle 14 in accordance with its rotation about its own axis to change their positions relative to the pedal 18. When the pedal 18 makes one complete rotation in a circle as shown in FIG. 4, his plantar arch is rubbed once by each of the projections 21 and the brush 23.

Figure 7:
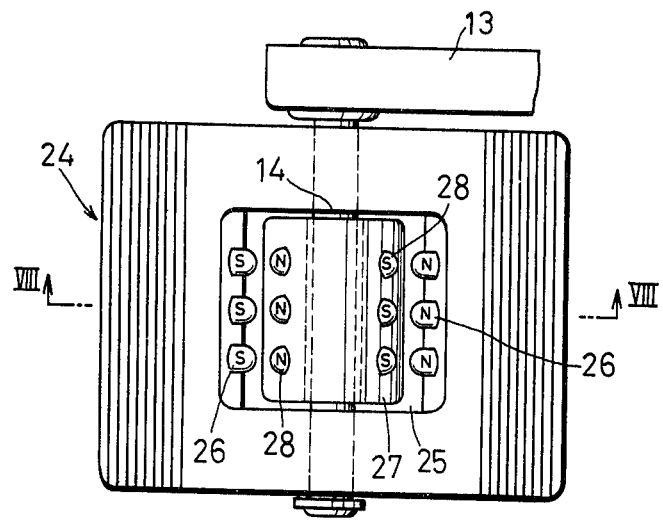
FIG. 7 is a fragmentary top plan view of a third embodiment of this invention.
Figure 8:
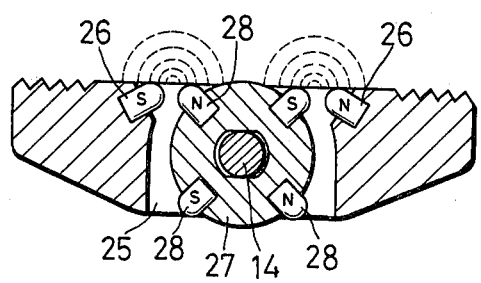
FIG. 8 is a fragmentary side elevational view partly in section of the device of FIG. 7.

A third embodiment of this invention, in which permanent magnets are employed instead of the projections 21 and the brush 23 of the second embodiment is described referring to FIGS. 7 and 8. In these Figures, a pedal 24 is rotatably mounted on the pedal spindle 14 and a rectangular bore 25 is formed in the center of the pedal 24. Three mutually spaced-apart permanent magnets 26 are set in a line, embedded in and obliquely project from each of the front and rear edges of the rectangular bore 25 as shown in FIG. 8. All of the three permanent magnets 26 in the front edge (left in FIG. 7) of the rectangular bore 25 have their S pole exposed, while all of the three permanent magnets 26 in the rear edge (right in FIG. 7) of the rectangular bore 25 have their N pole exposed. A cylindrical rotor 27 is provided within the rectangular bore 25 of the pedal 24 and fixed to the pedal spindle 14. Four groups of permanent magnets 28 are embedded in the outer peripheral surface of the rotor 27 and equally spaced from one another around the rotor 27. Each group consists of three magnets 28 arranged in a line and projecting from the outer peripheral surface of the rotor 27 perpendicularly thereto. The six magnets 28 in two diametrically opposite groups have their S poles projecting from the rotor 27, while the other six magnets 28 have their N poles projecting from the rotor 27. Each permanent magnet 28 is so positioned that during rotation of the rotor 27, it periodically approaches one of the permanent magnets 26 mounted on the pedal 24. Each and every permanent magnet 26 and 28 has a round projecting head. When the pedal 24 is in its highest position corresponding to the "A" position of FIG. 3, in which the relative position of the various parts of the device is as shown in FIG. 8, lines of magnetic force pass between the S poles of the permanent magnets 26 and the N poles of the permanent magnets 28 and between the N poles of the permanent magnets 26 and the S poles of the permanent magnets 28 as shown by broken lines in FIG. 8. Accordingly, if a man places his sole on the pedal 24, the magnetic force affects the skin of his sole and penetrates into his foot.

In operation, when a man treads the pedal 24 to rotate it in the same manner as in the second embodiment, the rotor 27 rotates with the pedal spindle 14. Accordingly, the permanent magnets 28 on the rotor 27 rub the sole of his foot to give a mechanical massaging effect thereto. As the pedal 24 is stepped down to further rotate the rotor 27, the S poles of three permanent magnets 28 are brought face to face with the S poles of the front three permanent magnets 26 and the N poles of three permanent magnets 28 approach the N poles of the rear three permanent magnets 26 to cause change in the direction of the lines of magnetic force.

It will, thus, be understood that when a man steps down the pedals 24 and rotates them over and over again, the soles of his feet are not only mechanically massaged by the permanent magnets 28 on the rotor 27, but are also magnetically affected so that the magnetic fields developed between permanent magnets 26 and 28 and periodically repeated changes in the direction of magnetic force stimulate the action of the blood vessels in the feet to promote the circulation of the blood. It is to be understood that the number and arrangement of the permanent magnets provided on the pedal and the rotor are not limited to those shown in FIGS. 7 and 8.

What is claimed is:

1. A rotary foot-operated massaging device comprising a horizontal shaft rotatable about its own axis, a pair of cranks each having one end secured to one end of said shaft, a pedal spindle having one end secured to the other end of said each crank at right angles thereto, a pedal rotatably mounted on each of said pedal spindles, massage means supported on at least said each pedal spindle for rotation therewith to intermittantly massage the sole of a foot placed on said each pedal, and said massage means includes eccentric pins fastened to said pedal spindles at the ends remote from said cranks so that said pins rotate around said pedal spindles and roller means overlying said eccentric pins to intermittantly engage the foot when said foot overlies the roller means.

2. A rotary foot-operated massaging device as set forth in claim 1, wherein said pin has an axis which is parallel to the axis of said pedal spindle.

3. A rotary foot-operated massaging device as set forth in claim 1, wherein said pin has an axis disposed at an angle to the axis of said pedal spindle.

4. A rotary foot-operated massaging device as set forth in claim 3, wherein said device is associated with an ordinary bicycle with its bracket axle serving as said horizontal shaft.

5. A rotary foot-operated massaging device comprising a horizontal shaft rotatable about its own axis, a pair of cranks each having one end secured to one end of said shaft, a pedal spindle having one end secured to the other end of said each crank at right angles thereto, a pedal rotatably mounted on each of said pedal spindles, massage means supported on at least said each pedal spindle for rotation therewith to intermittantly massage the sole of a foot placed on said each pedal, and a comb-like structure extending from said supporting means and along said spindle, said structure being rotable with rotation of said horizontal shaft.

6. A rotary foot-operated massaging device as set forth in claim 5, wherein said comb-like structure comprises a plurality of slender projections gradually increasing in length toward said one end of said pedal spindle.

7. A rotary foot-operated massaging device as set forth in claim 6, wherein said massaging means further comprises a brush disposed along said pedal spindle and gradually increasing in width toward said one end of said pedal spindle, said brush extending in a direction diametrically opposite to said projections.

8. A foot-operated massaging device as set forth in claim 7, wherein said each pedal comprises a pair of spaced-apart pedal elements parallel to said pedal spindle and a pair of spaced-apart leaf springs perpendicular to said pedal spindle and connected to said pedal elements to form a rectangular frame in which said massaging means and said supporting means are positioned rotatably relative to said pedal which is rotatably supported on said pedal spindle by said leaf springs.

9. A rotary foot-operated massaging device as set forth in claim 8, wherein said device further includes a portable and floor-mountable supporting structure on which said horizontal shaft is supported.

10. A rotary foot-operated massaging device comprising a horizontal shaft rotatable about its own axis, a pair of cranks each having one end secured to one end of said shaft, a pedal spindle having one end secured to the other end of said each crank at right angles thereto, a pedal rotatably mounted on each of said pedal spindles, massage means supported on at least said each pedal spindle for rotation therewith to intermittantly massage the sole of a foot placed on said each pedal, and said each pedal comprising a hollow rectangular structure having a rectangular bore in its center; said supporting means comprises a cylindrical rotor secured about said each pedal spindle and having an outer diameter substantially equal to the depth of said bore; and said massaging means comprises a plurality of permanent magnets projecting radially from the outer peripheral surface of said rotor.

11. A rotary foot-operated massaging device as set forth in claim 10, wherein said permanent magnets are grouped into a plurality of groups equally spaced around said outer peripheral surface of said rotor, each of said groups comprising a plurality of permanent magnets arranged in a line parallel to said pedal spindle and having exposed ends of the same polarity which is reverse to the polarity of exposed ends of the magnets of any immediately adjoining group.

12. A rotary foot-operated massaging device as set forth in claim 11, wherein said massaging means further comprises a plurality of permanent magnets partly embedded in said pedal along each of a pair of opposite edges of said bore which are parallel to said rotor, each of said last mentioned magnets projecting obliquely at an angle to the upper surface of said pedal.

13. A rotary foot-operated massaging device as set forth in claim 12, wherein the number of said last mentioned magnets on each of said edges of said bore being equal to the number of said first mentioned magnets composing one of said groups, said magnets on one of said edges having exposed ends of polarity different from that of exposed ends of said magnets on the other of said edges.

14. A rotary foot-operated massaging device as set forth in claim 13, wherein said device further includes a portable and floor-mountable supporting structure on which said horizontal shaft is supported.

* * * * *

UNITED STATES PATENT AND TRADEMARK OFFICE
CERTIFICATE OF CORRECTION

PATENT NO. : 4,150,667
DATED : April 24, 1979
INVENTOR(S) : Toshio Takeuchi

It is certified that error appears in the above—identified patent and that said Letters Patent are hereby corrected as shown below:

Claim 8, line 1 before "foot-operated" insert rotary.

Signed and Sealed this

Thirtieth Day of October 1979

[SEAL]

Attest:

RUTH C. MASON
Attesting Officer

LUTRELLE F. PARKER
Acting Commissioner of Patents and Trademarks